United States Patent [19]

Hunt

[11] 4,245,640
[45] Jan. 20, 1981

[54] CHEST MOTION ELECTRICITY GENERATING DEVICE

[76] Inventor: Robert J. Hunt, 5009 Green Mountain Rd., Columbia, Md. 21044

[21] Appl. No.: 840,237

[22] Filed: Oct. 7, 1977

[51] Int. Cl.² ............................................. A61N 1/00
[52] U.S. Cl. .................................................. 128/419 B
[58] Field of Search ............ 128/2 P, 2 R, 2 S, 2.08, 128/2.1 R, 419 B, 419 RS, 419 R; 3/1.1

[56] References Cited

U.S. PATENT DOCUMENTS

| 2,547,106 | 12/1970 | Bornmann | 128/2 S |
| 3,268,845 | 8/1966 | Whitmore | 128/2 S |

FOREIGN PATENT DOCUMENTS

| 11107 | of 1910 | United Kingdom | 128/419 B |
| 456311 | 11/1936 | United Kingdom | 128/419 R |

OTHER PUBLICATIONS

Myers et al., "American Journal of Medical Electronics," Oct.–Dec. 1964, pp. 233–236.

Primary Examiner—William E. Kamm
Attorney, Agent, or Firm—Oblon, Fisher, Spivak, McClelland & Maier

[57] ABSTRACT

A self-contained chest motion electricity generating device which converts normal respiratory breathing motion into electrical energy. The device employs a magnetic circuit which includes a permanent magnet and an induction coil wrapped around a ferromagnetic core. The magnetic circuit is mounted on a chest harness which includes shoulder straps and a chest strap. The chest strap includes an elastic materal which expands and contracts with normal respiratory motion. The permanent magnet and the induction coil of the magnetic circuit is separated by the elastic material such that in the totally exhaled state, a minimal gap exists between the permanent magnet and the ferromagnetic core. Normal breathing action expands and contracts the elastic material, thus varying the separation distance between the induction coil and the permanent magnet in such a fashion as to vary the magnetic flux linkage with the induction coil, thereby inducing a current through the coil. This induced current is then made available from leads attached to the induction coil as usable electrical power.

9 Claims, 4 Drawing Figures

CHEST MOTION ELECTRICITY GENERATING DEVICE

BACKGROUND OF THE INVENTION

1. Field of the Invention

This invention generally relates to electricity generators deriving power from the chest motion of a human being.

2. Description of the Prior Art

As a result of recent advances in the fields of medicine and electronic circuitry, a demand has arisen for a self-contained low-power electric generating device. Such a device today finds considerable application for any one of a number of body-attached mechanisms which use electric power. For example, cardiac pacemakers, electronic watches, hearing aids, and the like are all generally powered by small batteries. In the past, these batteries have usually been non-rechargeable, therefore requiring periodic replacement. Replacement of these batteries, however, is at best inconvenient, and in the case of cardiac pacemakers involves serious surgery. Accordingly, at least as far as cardiac pacemakers are concerned, the trend has been to provide chargeable batteries in conjunction with battery-charging means as the energy source for the pacemaker.

One such self-powered pacemaker, as shown in U.S. Pat. No. 3,943,936 to Rasor et al, discloses a self-powered pacemaker device energized by a nucleonic battery in conjunction with a battery-charging device. This device is implanted into the heart ventricle, whereby the battery charger derives its power from movement of the heart. While this device may be satisfactory for its intended application, it can only be implanted or replaced by major open heart surgery, and therefore entails considerable risk. Furthermore, because of its unique implanting arrangement, this self-powered pacer is subject to reduced power output requirements to reliably produce consistent pacing. As a result, its potential power capacity would be insufficient for other electrical power applications.

While chest motion electrical generators have been known in the prior art, these generators have been used merely to monitor respiratory movements. Examples of these devices are found in U.S. Pat. Nos. 3,268,845 and 3,782,368. In view of the respiratory transducers disclosed in these patents, energy is consumed instead of generated, and these devices find no application as battery charging devices.

SUMMARY OF THE INVENTION

Accordingly, one object of this invention is to provide a novel electricity generating device.

Another object of this invention is to provide an electricity generating device which derives its power from the respiratory chest motion of the human body.

A further object of this invention is to provide a chest motion electricity generating device which provides an electrical output suitable for charging rechargeable batteries.

Still another object of this invention is to provide a chest motion electricity generating device for use in charging the batteries of an appliance associated or attached to the human body.

Furthermore, an additional object of this invention is to provide a chest motion electricity generating device for use with a cardiac pacemaker, an electronic watch, or a hearing aid.

These and other objects of the present invention are achieved by providing a self-contained chest motion electricity generating device which converts normal respiratory breathing motion into eletrical energy. The device employs a magnetic circuit which includes a permanent magnet and an induction coil wrapped around a ferromagnetic core. The magnetic circuit is mounted on a chest harness which includes shoulder straps and a chest strap. The chest strap includes an elastic material which expands and contracts with normal respiratory motion. The permanent magnet and the induction coil of the magnetic circuit is separated by the elastic material such that in the totally exhaled state, a minimal gap exists between the permanent magnet and the ferromagnetic core. Normal breathing action expands and contracts the elastic material, thus varying the separation distance between the induction coil and the permanent magnet in such a fashion as to vary the magnetic flux linkage with the induction coil, thereby inducing a current through the coil. This induced current is then made available from leads attached to the induction coil as usable electrical power.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
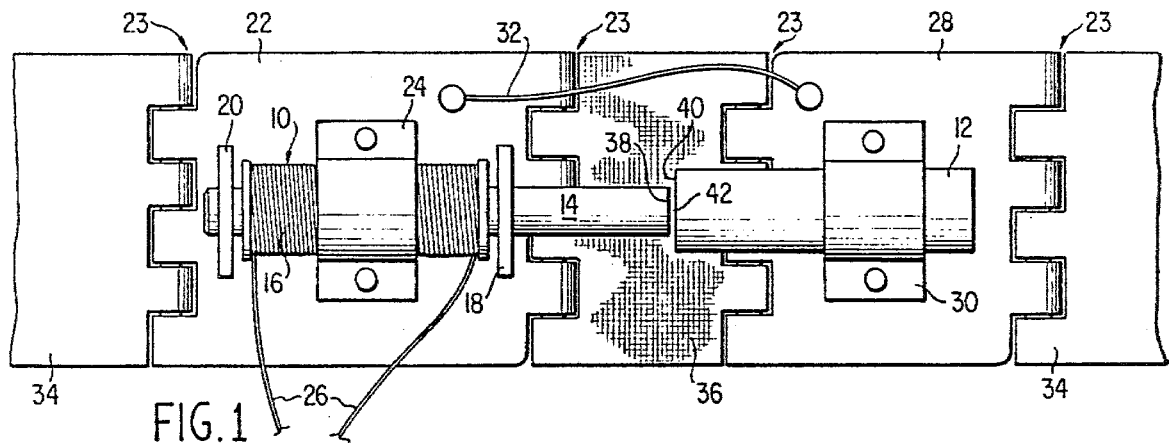
FIG. 1 is a detailed view of the magnetic circuit of the chest motion electricity generating device.

Referring now to the drawings wherein like reference numerals designate identical or corresponding parts throughout the several views, and more particularly to FIG. 1 thereof, the magnetic circuit of the chest motion electricity generating device includes an induction coil 10 and a permanent magnet 12. The induction coil 10 is composed of a ferromagnetic core 14 consisting of materials such as iron, cobalt, or nickel. Conducting wire 16 is wrapped around the ferromagnetic core 14. End plates 18 and 20 made of a diamagnetic material are provided on either end of the induction coil 10. The induction coil 10 is fastened to a mounting plate 22 by fastener 24. Leads 26, which carry the induced EMF voltage output, are provided at either er, 1 of the induction coil 10.

The permanent magnet 12, which is of conventional type, is attached to a mounting plate 28 by means of a fastener 30. The mounting plates 22 and 28 which respectively carry the induction coil 10 and the permanent magnet 12 are attached to a stiff strap 34 made of leather, plastic, coated fiber, or the like, by means of hinges 23. Mounting plates 22 and 28 are also hingedly attached to elastic material 36 which separates mounting plates 22 and 28. The width of the elastic material 36 is designed such that in its unstretched condition, a narrow gap 42 is formed between the tip 38 of end plate 18 and the end 40 of permanent magnet 12. Upon normal breathing movement, the elastic separator 36 expands and contracts, thereby varying the width of gap 42, and accordingly varying the magnetic coupling between the induction coil 10 and the permanent magnet 12. The elastic separating material 36 is conventionally made of elastic yarn consisting of, for example, rubber, spandex or anidex fibers, as is used for expansion belts, garters, suspenders, etc. Otherwise, elastic springs or high tensile steel straps, which elongate upon inhalation, can also be used for the elastic material 36. Also, as shown in FIG. 1, control cable 32 is attached to mounting plates 22 and 28 and limits the maximum separation of these mounting plates.

Figure 2:
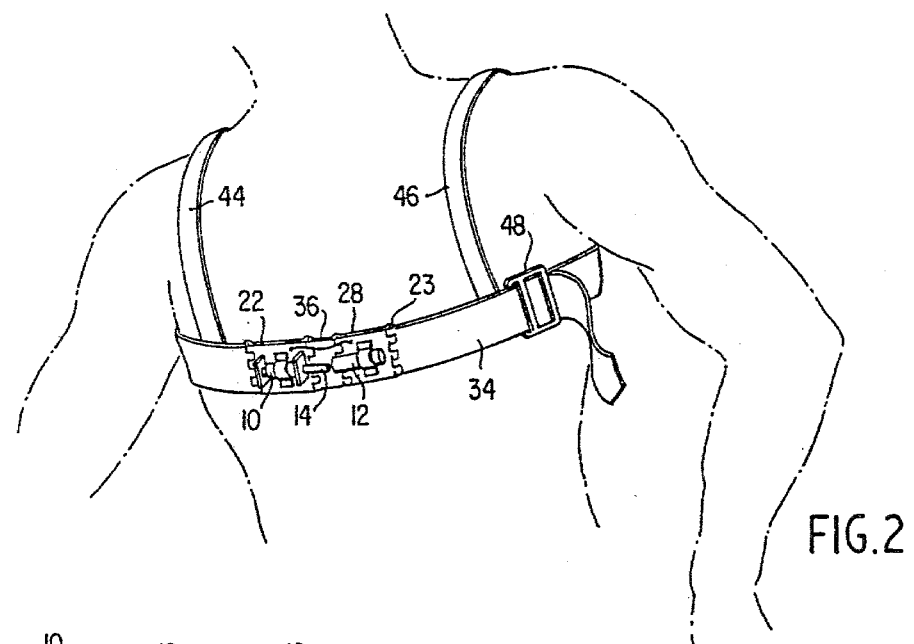
FIG. 2 is a view of the electricity generating device mounted on a chest harness and worn by a perspective human user thereof.

As seen in FIG. 2, the chest motion electric generating device of this invention is mounted on a harness 44 which is worn by the human user. Harness 44 includes a chest strap 34 which is connected by the elastic material 36. Attached to the harness 44 are over-the-shoulder straps 46. Also provided is a buckel 48 for adjusting the strap 34 snuggly around the chest of the wearer. Optionally, adjustment buckels can also be provided for shoulder straps 46.

The operation of the chest motion electric generating device is now described. The chest harness 44 is attached to the human body as shown in FIG. 2. Buckel 48 is adjusted such that upon total exhalation a minimum gap 42 exists between the tip 38 of end plate 13 of induction coil 10 and the end 40 of permanent magnet 12. Thereafter, as the lungs and chest of the person wearing the device expands and contracts, the elastic material 36 likewise expands and contracts, thereby varying the magnetic coupling between the induction coil 10 and the permanent magnet 12. In accordance with Faradays Law, an induced EMF is generated, the absolute magnitude of which is dependent upon the number of turns of the conducting wire 16 of induction coil 10 and the rate of change of the magnetic flux through the conduction coil 10. This induced EMF is evident across leads 26, and can be applied to conventional battery charging circuits. Since the polarity of the EMF induced across the induction coil 10 changes upon a reversal of the relative motion between induction coil 10 and permanent magnet 12, a full-wave rectifier bridge is a potential candidate as a battery charging circuit.

Figure 3A:
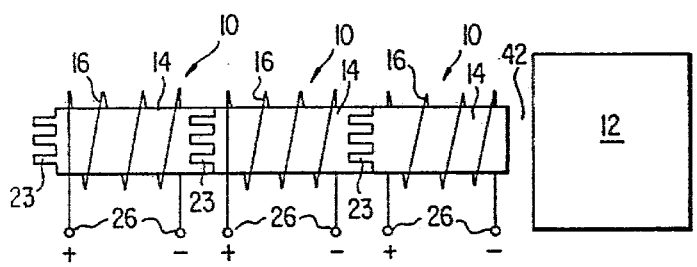
FIGS. 3A and 3B are schematic views of several embodiments of the present invention utilizing different electrical and/or magnetic circuit arrangements.

As shown in FIG. 3, the chest motion electricity generating device of this invention can be arranged in any one of a number of configurations. In the embodiment of FIG. 3A, a plurality of induction coils 10, each with separate conductor coils 16 and ferromagnetic cores 14, are separated by gaps 42. Each induction coil 10 and the permanent magnet 12 is mounted on a mounting plate. Adjacent induction coil mounting plates are once again connected by hinges 23, and as in FIG. 1, an elastic separating material 36 is provided between an induction coil mounting plate, and the permanent magnet mounting plate. The plurality of discrete induction coils 10 are provided to promote mechanical flexibility when attached to the chest harness. The leads 26 from each of the induction coils can be electrically connected in series or in parallel, depending upon the voltage and current requirements of the battery to be charged. Likewise, the induction coils 10 can be arranged in any combination of series and parallel connections to provide the requisite electrical output.

Figure 3B:
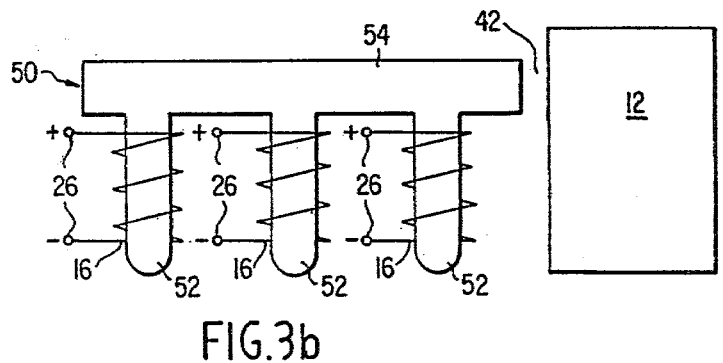

As shown in the embodiment of FIG. 3B, the ferromagnetic core 50 also may include a horizontal arm 54 from which legs 52 append. A plurality of conductor coils 16 are each wrapped around the legs 52 of the common ferromagnetic core 50. Ferromagnetic core 50 and magnet 12 are again mounted on mounting plates which are hingedly connected to the expandable elastic material. Upon normal breathing motion, the gap 42 between the horizontal arm 54 of ferromagnetic core 50 and magnet 12 increases and decreases, thereby generating the varying magnetic flux which induces the EMF across conductor coils 26. The embodiment of FIG. 3B advantageously reduces the number of air gaps 42 relative to the embodiment of FIG. 3A, and thereby promotes improved magnetic coupling between the magnet 12 and conductor coils 16. Furthermore, the embodiment of FIG. 3B achieves its improved magnetic coupling with minimal mechanical disadvantage because of the physically parallel orientation of conductor coil 16. As in the embodiment of FIG. 3A, the leads 26 of the plurality of conductor coils 16 can be connected and in any requisite series or parallel combination, thereby optimizing the electrical performance of the chest motion electricity generating device.

As is noted above, the chest motion electricity generating device of this invention advantageously derives an electric current from normal human respiratory movement that can be used for battery charging or any other purpose. This current can advantageously be used, for example, to recharge batteries used as power sources for body attached electrical appliances. The chest motion electricity generating device of the invention is attached externally to the body of the user thereof, and is therefore conveniently made operational without the necessity of surgical procedures. Furthermore, the mounting arrangement for the chest motion electrical generating device is designed to promote mechanical comfort and electrical flexibility. Unlike the electrical generating devices of the prior art, the chest motion electricity generator or transducer of this invention is amenable to a modular building block configuration which promotes electrical compatability with any of a number of presently marketed body attached electrical appliances.

Obviously, additional modifications and variations of the present invention are possible in light of the above teachings. In particular, the electricity generating device of this invention can be mounted in environment other than that as discussed above. For example, the device can be mounted on the wheels of a bicycle in such a way that the rotary motion of the wheels causes the necessary separation and contraction of the elastic material separating the induction coil and the magnet. The resulting electrical current produced can then be used to charge the battery of an auxiliary electrical device attached to the bicycle, such as a horn, headlight, or the like. In that regard, the electricity generating device of the present invention can be modified to work in conjunction with virtually any mechanically dynamic device whose movement undergoes a direction reversal. It is therefore to be understood that within the scope of the appended claims, the invention may be practiced otherwise than as specifically described herein.

What is claimed as new and desired to be secured by Letters Patent of the United States is:

1. A chest motion electricity generating device comprising:

magnetic flux generating means;

induction coil means, said magnetic flux generating means and said induction coil means forming a magnetic circuit;

an elastic separator connected to said magnetic flux generating means and said induction coil means, said elastic separator located between said magnetic flux generating means and said induction coil means;

non-elastic chest harness means which includes at least one adjustable chest strap for surrounding the circumference of the human chest, said chest strap provided with two ends, said two ends respectively attached to said magnetic flux generating means and said induction coil means;

whereby normal respiratory motion causes expansion and contraction of said elastic separator, said respiratory motion thereby changing the magnetic flux linkage between said magnetic flux generating means and said induction coil means, and thereby generating an induced EMF across said induction coil means, said induced EMF being made available as useful electrical energy.

2. A chest motion electricity generating device according to claim 1 wherein said magnetic flux generating means comprises:

a permanent magnet mounted on a diamagnetic magnet mounting plate and attached to said mounting plate by fastening means.

3. A chest motion electricity generating device according to claim 1 wherein said induction coil means comprises:

electrical current conducting wire wrapped around a ferromagnetic core, said wire having electrical output leads, and said wire wrapped core mounted on a diamagnetic induction coil mounting plate and held thereon by fastening means.

4. A chest motion electricity generating device according to claim 1 wherein said elastic separator comprises:

an elastic yarn from the group consisting of rubber, spandex, or anidex fibers.

5. A chest motion electricity generating device according to claim 1 wherein said elastic separator comprises:

elastic springs

6. A chest motion electricity generating device according to claim 1 wherein said elastic separator comprises:

high tensile steel straps.

7. A chest motion electricity generating device according to claim 1 wherein said non-elastic chest harness comprises:

adjustable shoulder straps, and at least one adjustable chest strap connected to said shoulder straps, said chest strap worn around the circumference of the human body and including two ends, said two ends respectively attached to said magnetic flux generating means and said induction coil means.

8. A chest motion electricity generating device according to claim 1 wherein said induction coil means comprises:

a plurality of electrical current conducting wires respectively wrapped around a plurality of ferromagnetic cores, each of said ferromagnetic cores mounted on respective diamagnetic mounting plates, said plurality of mounting plates hingedly connected to promote mechanical flexibility.

9. A chest motion electricity generating device according to claim 1 in which said induction coil means comprises:

a ferromagnetic core with a horizontal arm and a plurality of perpendicular legs appending from said arm, a plurality of electricity conducting wires respectively wrapped around each of said perpendicular legs of said ferromagnetic core, each of said wires having output leads which can be connected in any desired electrical configuration, a diamagnetic mounting plate on which said wire wrapped ferromagnetic core is mounted, and fastening means for attaching said wire wrapped ferromagnetic core to said mounting plate.

* * * * *